United States Patent
Mandell et al.

(10) Patent No.: US 6,229,062 B1
(45) Date of Patent: May 8, 2001

(54) SUPERABSORBENT POLYMER CONTAINING ODOR CONTROLLING COMPOUNDS AND METHODS OF MAKING THE SAME

(75) Inventors: Kathleen Mandell, West Chicago; Jerald W. Darlington, Jr., Marengo; Anthony S. Tomlin, Island Lake, all of IL (US)

(73) Assignee: BASF Aktiengesellschaft Corporation, Ludwigshafen (DE)

( * ) Notice: Subject to any disclaimer, the term of this patent is extended or adjusted under 35 U.S.C. 154(b) by 0 days.

(21) Appl. No.: 09/301,634

(22) Filed: Apr. 29, 1999

(51) Int. Cl.$^7$ ........................................ A61L 15/42
(52) U.S. Cl. .......................... 604/367; 604/358; 604/359
(58) Field of Search ..................... 604/367, 358

(56) References Cited

U.S. PATENT DOCUMENTS

| | | | |
|---|---|---|---|
| 4,401,712 | 8/1983 | Morrison | 428/289 |
| 4,471,871 | 9/1984 | Rockliffe et al. | 206/205 |
| 4,494,482 | 1/1985 | Arnold | 119/1 |
| 4,842,593 | 6/1989 | Jordan et al. | 604/360 |
| 4,985,023 | 1/1991 | Blank et al. | 604/360 |
| 4,990,338 | 2/1991 | Blank et al. | 424/443 |
| 5,300,565 | * 4/1994 | Berg et al. | 525/54.2 |
| 5,419,956 | * 5/1995 | Roe | 428/283 |
| 5,422,169 | * 6/1995 | Roe | 428/212 |
| 5,429,628 | 7/1995 | Trinh et al. | 604/359 |
| 5,595,731 | 1/1997 | Vallieres | 424/76.4 |
| 5,714,445 | 2/1998 | Trinh et al. | 510/103 |
| 5,733,272 | 3/1998 | Brunner et al. | 604/359 |
| 5,777,003 | 7/1998 | Haas et al. | 523/223 |

FOREIGN PATENT DOCUMENTS

| | | | |
|---|---|---|---|
| 0 850 615 | 7/1998 | (EP) | A61F/13/15 |
| WO 97/09354 | 3/1997 | (WO) | C08F/2/16 |
| WO 98/56342 | * 12/1998 | (WO) | 604/359 |
| WO 99/64485 | 12/1999 | (WO) | C08F/20/04 |

OTHER PUBLICATIONS

Nissen et al., "Triclosan, an antimicrobial active ingredient with anti–inflammatory activity," *Cosmetics & Toiletries*, vol. 113, p. 61, 1993.

Anonymous, product bulletin, "Technical Information of FAVOR Z 1079," Stockhausen GmbH & Co., Krefeld, Germany (Jan., 1999).

* cited by examiner

*Primary Examiner*—John G. Weiss
*Assistant Examiner*—Michael Bogart
(74) *Attorney, Agent, or Firm*—Marshall, O'Toole, Gerstein, Murray & Borun

(57) ABSTRACT

An odor-controlling superabsorbent polymer and methods of manufacturing the odor-controlling superabsorbent polymer are disclosed. The odor-controlling superabsorbent polymer has an odor-controlling compound homogeneously distributed therein. The odor-controlling compound is a material selected from the group consisting of a cyclodextrin compound, an amphoteric surfactant, a water-insoluble phosphate, triclosan, and mixtures thereof.

48 Claims, No Drawings

SUPERABSORBENT POLYMER CONTAINING ODOR CONTROLLING COMPOUNDS AND METHODS OF MAKING THE SAME

BACKGROUND OF THE INVENTION

1. Field of the Invention

The present invention generally relates to superabsorbent polymers (SAPs) containing odor-controlling compounds. The odor-controlling SAPs can be incorporated into articles, such as bandages, diapers, sanitary napkins, and other disposable paper products, where the odor-controlling compounds act to reduce and/or eliminate malodors.

BRIEF DESCRIPTION OF RELATED TECHNOLOGY

Water-absorbing resins are widely used in sanitary and hygienic goods, wiping cloths, water-retaining agents, dehydrating agents, sludge coagulants, disposable towels and bath mats, disposable door mats, thickening agents, disposable litter mats for pets, condensation-preventing agents, and release control agents for various chemicals. Water-absorbing resins are available in a variety of chemical forms, including substituted and unsubstituted natural and synthetic polymers, such as hydrolysis products of starch acrylonitrile graft polymers, carboxymethylcellulose, crosslinked polyacrylates, sulfonated polystyrenes, hydrolyzed polyacrylamides, polyvinyl alcohols, polyethylene oxides, polyvinylpyrrolidones, and polyacrylonitriles.

Such water-absorbing resins are termed "superabsorbent polymers," or SAPs, and typically are lightly crosslinked hydrophilic polymers. SAPs are discussed generally in Goldman et al. U.S. Pat. Nos. 5,669,894 and 5,559,335, the disclosures of which are incorporated herein by reference. SAPs can differ in their chemical identity, but all SAPs are capable of absorbing and retaining amounts of aqueous fluids equivalent to many times their own weight, even under moderate pressure. For example, SAPs can absorb one hundred times their own weight, or more, of distilled water. The ability to absorb aqueous fluids under a confining pressure is an important requirement for an SAP used in a hygienic article, such as a diaper.

As used herein, the term "SAP particles" refers to superabsorbent polymer particles in the dry state, more specifically, particles containing from no water up to an amount of water less than the weight of the particles. The terms "SAP gel," "SAP hydrogel," or "hydrogel" refer to a superabsorbent polymer in the hydrated state, more specifically, particles that have absorbed at least their weight in water, and typically several times their weight in water.

Bodily fluids, such as blood, urine, menses, and the like, have an unpleasant odor or develop an unpleasant odor when exposed to air and/or bacteria for prolonged time periods. For example, it is known that human urine contains urea, which in turn is hydrolyzed to yield carbon dioxide and ammonia, the latter having a pungent, unpleasant odor. Ammonia also is an alkaline substance that can irritate skin. Once these bodily fluids are absorbed by the hygienic and sanitary goods containing an SAP, it is important to ensure proper odor control, for example by overcoming the malodor and irritation caused by ammonia, or by preventing the formation of ammonia. Prevention of ammonia formation can be accomplished by inhibiting the action of urease, an enzyme produced by bacteria that catalyzes the hydrolysis of urea to ammonia and carbon dioxide.

For example, cyclodextrin has been found to be an effective compound for controlling malodors. Cyclodextrin is capable of encapsulating molecules, and, therefore, as a dry powder, effectively absorbs odoriferous molecules into its structure. When wet by bodily fluids, cyclodextrin is solubilized, and then is capable of controlling malodors more effectively by forming inclusion complexes with the odoriferous molecules (e.g., ammonia) or precursors thereof (e.g., urea). For example, cyclodextrin, when wet by urine, encapsulates urea and acts as a barrier preventing the catalytic hydrolysis of urea to ammonia by urease. Furthermore, any ammonia formed by the noncatalytic hydrolysis of urea is encapsulated by the cyclodextrin, thereby trapping the malodorous ammonia molecules.

U.S. Pat. Nos. 5,733,272, 5,714,445, and 5,429,628 disclose that cyclodextrin can be incorporated with SAPs by sprinkling, mixing, or distributing a dry cyclodextrin powder onto a fluid absorbent material, e.g., an SAP. More specifically, the patents disclose that cyclodextrin can be distributed by an in situ crystallization technique wherein the fluid absorbent material is impregnated with a saturated aqueous solution of the cyclodextrin. Upon drying, the cyclodextrin crystallizes as small particles adhering to the absorbent material. This process is carried out, for example, by spraying an aqueous solution of the cyclodextrin onto an already formed dry absorbent material, or onto a wet fiber web precursor of the dry absorbent material. Alternatively, the patents disclose that a water-soluble binder can be used to adhere cyclodextrin powder to the fluid absorbent material.

The distribution of cyclodextrin as disclosed in these patents, however, is not uniform throughout a cross section of the absorbent material. A major portion of the cyclodextrin is present near the external surface of the absorbent material (e.g., SAP particle), and a minor portion, if any, of the cyclodextrin is present within the absorbent material particle. When an absorbent material is wet by bodily fluids, the fluids typically penetrate beyond the surface of the absorbent material and soak into the core of the material. With an inadequate amount of cyclodextrin at or near the core of the material (e.g., SAP particle), malodors cannot be controlled or trapped effectively.

Therefore, it would be desirable to provide an SAP that exhibits exceptional odor-reducing and odor-controlling characteristics. Furthermore, it would be desirable to provide an SAP having a uniform distribution of an odor-controlling compound therein. In addition, it would be desirable to provide an odor-controlling SAP that has an ability to absorb liquids quickly, demonstrates good fluid permeability and conductivity into and through the SAP, and has a high gel strength, such that the hydrogel formed from the SAP does not deform or flow under an applied stress or pressure.

SUMMARY OF THE INVENTION

The present invention is directed to an odor-controlling superabsorbent polymer (SAP) and to methods of manufacturing an odor-controlling SAP. More particularly, the present invention is directed to an odor-controlling SAP having an odor-controlling compound homogeneously distributed throughout an SAP particle.

One aspect of the present invention, therefore, is to provide a method of manufacturing an odor-controlling SAP including the steps of polymerizing an α,β-unsaturated carboxylic acid, such as acrylic acid, either neutralized, unneutralized, or a mixture of both (i.e., DN (degree of neutralization) of 0 to 100), to form a polymeric hydrogel, admixing an odor-controlling compound selected from the group consisting of a cyclodextrin compound, triclosan, an amphoteric surfactant, a water-insoluble phosphate, and mixtures thereof, with the polymeric hydrogel, and then, if necessary or desired, neutralizing the resulting admixture. The resulting odor-controlling hydrogel has the odor-controlling compound homogeneously dispersed throughout the hydrogel.

Another aspect of the invention is to provide a method of making an odor-controlling SAP including the steps of polymerizing a mixture containing water, an α,β-unsaturated carboxylic acid (either neutralized, unneutralized, or a mixture of both), and an odor-controlling compound selected from the group consisting of a cyclodextrin compound, an amphoteric surfactant, a water-insoluble phosphate, and mixtures thereof, to form a polymeric hydrogel, and thereafter, if necessary or desired, neutralizing the polymeric hydrogel to form an odor-controlling SAP having an odor-controlling compound distributed homogeneously therethrough. The method also includes the optional step of admixing a second odor-controlling compound selected from the group consisting of a cyclodextrin compound, triclosan, an amphoteric surfactant, a water-insoluble phosphate, and mixtures thereof, with the polymeric hydrogel.

In accordance with another aspect of the present invention, the hydrogel prepared by either of the two above-described methods is dried, then formed or sized into SAP particles having an odor-controlling compound homogeneously distributed throughout the particles. The odor-controlling SAP particles can be incorporated into articles used to absorb liquids, like diapers and catamenial devices.

Further aspects and advantages of the invention will become apparent to those skilled in the art from a review of the following detailed description of the invention, taken in conjunction with the examples and the appended claims.

DETAILED DESCRIPTION OF THE INVENTION

The present invention is directed to an odor-controlling SAP having an odor-controlling compound distributed homogeneously throughout the SAP. The odor-controlling SAP is prepared by a method comprising the steps of polymerizing a mixture of (a) water and (b) an α,β-unsaturated carboxylic acid, either neutralized or unneutralized, or a mixture thereof, to form a polymeric hydrogel, admixing an odor-controlling agent selected from the group consisting of a cyclodextrin compound, triclosan, an amphoteric surfactant, a water-insoluble phosphate, and mixtures thereof, with the polymeric hydrogel to homogeneously disperse the odor-controlling compound in the hydrogel, and then, if necessary or desired, neutralizing the resulting admixture.

Alternatively, the odor-controlling SAP is prepared by a method including the steps of polymerizing a mixture containing (a) water, (b) an α,β-unsaturated carboxylic acid, either neutralized or unneutralized, or a mixture thereof, and (c) an odor-controlling compound selected from the group consisting of a cyclodextrin compound, an amphoteric surfactant, a water-insoluble phosphate, and mixtures thereof, to form a polymeric hydrogel having the odor-controlling compound homogeneously dispersed throughout the hydrogel, and thereafter, if necessary or desired, neutralizing the polymeric hydrogel. The method also can include the optional step of admixing a second odor-controlling compound selected from the group consisting of a cyclodextrin compound, triclosan, an amphoteric surfactant, a water-insoluble phosphate, and mixtures thereof, with the polymer hydrogel, either prior to or after the optional neutralization step.

The present odor-controlling SAPs are based on polymerized vinyl monomers, particularly α,β-unsaturated carboxylic acids, that have the ability to absorb several times its weight of a liquid. The remainder of the specification is directed to an SAP based on acrylic acid, however, other vinyl monomers and α,β-unsaturated carboxylic acids can be used in the odor-controlling SAPs of the present invention. Odor-controlling SAPs prepared by the present methods, which incorporate the present odor-controlling compounds, exhibit improved odor control properties regardless of the identity of the vinyl monomer and/or α,β-unsaturated carboxylic acid used to prepare the SAP.

The present odor-controlling SAPs can be anionic or cationic in nature. The anionic SAPs can be, for example, polyacrylic acid, hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, ethylene-maleic anhydride copolymers, isobutylene-maleic anhydride copolymers, poly(vinylsulfonic acid), poly(vinylphosphonic acid), poly(vinylphosphoric acid), poly(vinylsulfuric acid), sulfonated polystyrene, and mixtures thereof.

The cationic SAPs can be, for example, a poly(vinylamine), a poly(dialkylaminoalkyl (meth)acrylamide), a lightly crosslinked polyethylenimine, a poly(allylamine), a poly(allylguanidine), a poly(dimethyldiallylammonium hydroxide), a quaternized polystyrene derivative, such as

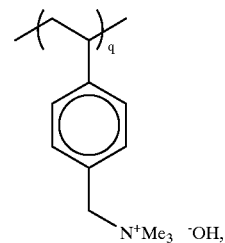

a guanidine-modified polystyrene, such as

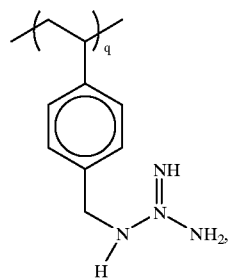

a quaternized poly((meth)acrylamide) or ester analog, such as

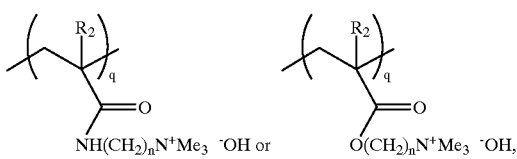

wherein Me is methyl, $R_2$ is hydrogen or methyl, n is a number 1 to 8, and q is a number from 10 to about 100,000, or a poly(vinylguanidine), i.e., poly(VG), a strong basic water-absorbing resin having the general structural formula

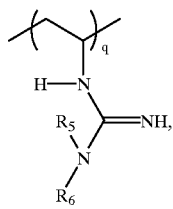

wherein q is a number from 10 to about 100,000, and $R_5$ and $R_6$, independently, are selected from the group consisting of hydrogen, $C_1$–$C_4$ alkyl, $C_3$–$C_6$ cycloalkyl, benzyl, phenyl, alkyl-substituted phenyl, naphthyl, and similar aliphatic and aromatic groups.

Therefore, the present invention is not limited to SAPs based on acrylic acid, but extends to preferred SAPs that include, but are not limited to, methacrylic acid, ethacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, fumaric acid, tricarboxyethylene, and maleic anhydride. Acrylic acid, i.e., $CH_2=CHCO_2H$, however, is the most preferred α,β-unsaturated carboxylic acid.

The acrylic acid is polymerized by standard free radical techniques. The odor-controlling compound is incorporated into the polyacrylic acid in such a manner that the odor-controlling compound is homogeneously (or uniformly) distributed through-out the SAP. More specifically, the odor-controlling ling compound is homogeneously (or uniformly) distributed throughout an SAP particle such that a cross-section of the SAP particle reveals that there is a substantially equal amount of odor-controlling compound at or near the core of the SAP particle and at or near the surface of the odor-controlling SAP particle. The odor-controlling compounds useful in the present invention are discussed in more detail below.

The cyclodextrin can be any of the known cyclodextrins such as, unsubstituted cyclodextrins containing from six to twelve glucose monomers, especially, alpha-, beta-, and gamma-cyclodextrins, and/or their derivatives, and/or mixtures thereof. The alpha-, beta-, and gamma-cyclodextrins contain 6, 7, and 8 glucose monomer units, respectively, arranged in a donut-shaped ring. The specific coupling and conformation of the glucose units give the cyclodextrins a rigid, conical molecular structure with a hollow interior of a specific volume. The "lining" defining the hollow interior, or cavity, is formed by hydrogen atoms and glycosidic bridging oxygen atoms rendering this surface hydrophobic. These cavities can be filled with all or a portion of an organic molecule of suitable size to form an "inclusion complex." Alpha-, beta-, and gamma-cyclodextrins are commercially available from, inter alia, American Maize-Products Company (Amaizo), Hammond, Ind.

Alpha-, beta-, and gamma-cyclodextrin solids, therefore, have a "cage-like" crystalline structure. The packing of these cyclodextrin molecules within the crystal lattice is such that the cavity of one cyclodextrin molecule is blocked off on both sides by adjacent cyclodextrins, thereby producing isolated and closed cavities. These molecular arrangements are described in Szejtli, J. *Industrial Applications of Cyclodextrins: in Inclusion Compounds.* Vol. 3, pp. 330–335 (1984), which is hereby incorporated herein by reference. In the dry state, the isolated cavities are not readily accessible to airborne vapors, unlike other open-celled porous adsorbents, such as activated carbon and zeolites. Therefore, surface area availability is important for an effective malodor control performance by uncomplexed cyclodextrin powder. However, upon solubilization of cyclodextrin by body fluids, the isolated cavities become available to form inclusion complexes with the odoriferous molecules. The availability of solubilized, uncomplexed cyclodextrin, therefore, improves odor control capability.

Cyclodextrin derivatives are disclosed in U.S. Pat. Nos.: 3,426,011; 3,453,257; 3,453,258; 3,453,259; 3,453,260; 3,553,191; 3,565,887; 4,535,152; 4,616,008; 4,638,058; 4,746,734; and 4,678,598, the disclosures of which are hereby incorporated herein by reference. Examples of cyclodextrin derivatives suitable for use in the present invention include methyl beta-cyclodextrin, hydroxyethyl beta-cyclodextrin, and hydroxypropyl beta-cyclodextrin of different degrees of substitution, commercially available from Amaizo, and from Aldrich Chemical Company, Milwaukee, Wis., for example. Water-soluble cyclodextrin derivatives are preferred cyclodextrin derivatives.

Individual cyclodextrins also can be linked together by using multifunctional agents to form oligomers and polymers, for example. An example of such materials is beta-cyclodextrin/-epichlorohydrin copolymers, commercially available from Amaizo and from Aldrich Chemical Company.

Preferably at least a major portion of the cyclodextrins is alpha-, beta- and/or gamma-cyclodextrins, more preferably alpha- and beta-cyclodextrins. An especially preferred cyclodextrin for use in the present invention is beta-cyclodextrin. It is also preferred to use mixtures of cyclodextrins. Such mixtures can absorb odors more effectively by complexing with a wider range of odor-iferous molecules. Some cyclodextrin mixtures are commercially available from, inter alia, Ensuiko Sugar Refining Company, Yokohama, Japan, for example.

A cyclodextrin present in the odor-controlling SAP has a particle size of about 25 to about 200 microns, preferably about 50 to about 150 microns, and more preferably about 75 to about 100 microns. The cyclodextrin typically is added as a solid either to the monomer mixture prior to polymerizing the acrylic acid, or to a hydrogel of the polyacrylic acid after polymerization of the acrylic acid. If the cyclodextrin is added as a solution, either to the monomer mixture or to the polymeric hydrogel, the cyclodextrin ultimately is present in the odor-controlling SAP as solid domains having a particle size of about 25 to about 200 microns.

To ensure a uniform distribution through-out an odor-controlling SAP particle, the cyclodextrin (or any of the other odor-controlling compounds described herein) can be added to the aqueous solution of acrylic acid or sodium acrylate prior to polymerization and/or can be admixed with an already-formed polyacrylic acid hydrogel, either prior to or after neutralization. Introduction of the cyclodextrin at one or more of these stages in the preparation of the odor-controlling SAP distributes the cyclodextrin throughout the polyacrylic acid, as opposed to simply coating the surface of the polyacrylic acid particle.

Regardless of whether the cyclodextrin is added to the monomer solution or to the post-polymerization hydrogel, or to both, the cyclodextrin is present in an amount of about 0.1 to about 10 wt. %, preferably about 1 to about 8 wt. %, more preferably about 3 to about 5 wt. %, based on the weight of the vinyl monomers present in the monomer mixture.

In addition to the cyclodexrin, an amphoteric surfactant, a water-insoluble phosphate, triclosan, or mixtures thereof can be the odor-controlling compound. These compounds are not capable of entrapping ammonia or urea like a cyclodextrin, but, it is theorized that these compounds control odor by absorbing ammonia, or by slowing and/or preventing the enzymatic action of urease, which in turn slows and/or prevents the formation of malodorous ammonia, and/or by killing microorganisms. Like a cyclodextrin, each of the amphoteric surfactant and the water-insoluble phosphate odor-controlling compounds can be present in an amount of about 0.1 to about 10 wt. %, preferably about 1 to about 8 wt. %, more preferably about 3 to about 5 wt. %, based on the weight of the vinyl monomers present in the monomer mixture. The triclosan can be present in an amount of about 0.1 to about 1 wt. %, preferably about 0.2 to about 0.8 wt. %, and most preferably about 0.3 to about 0.5 wt. %.

While the amphoteric surfactant and the water-insoluble phosphate can be present in the monomer mixture prior to polymerization and/or post-polymerization, the triclosan can be added only post-polymerization due to its relative instability during polymerization conditions.

Amphoteric surfactants suitable for use in the invention are described in J. Lynn Jr., et al. "Surfactants/Detergents," *Encyclopedia of Chemical Technology*, Vol. 23 (1997) pp. 530–532, the disclosure of which is incorporated herein by reference. Generally, amphoteric surfactants, also known as ampholytic and zwitterionic surfactants, contain both an acidic (e.g., carboxylic acid) group and a basic hydrophilic (e.g., amino) group, and exhibit good surface activity properties over a wide pH range.

Examples of amphoteric surfactants that can be included in the present composition include, but are not limited to, betaines, hydroxypropylsultaines, amine oxides, n-alkylaminopropionates, n-alkyliminodipropionates, phosphobetaines, phosphitaines, imidazolines, alkoamphopropionates, alkoamphocarboxypropionates, alkoamphopropylsulfonates, alkoamphoglycinates, alkoamphocarboxyglycinates, and mixtures thereof. Examples of specific amphoteric surfactants include, but are not limited to, cocamidopropyl betaine, lauramidopropyl betaine, coco/oleamidopropyl betaine, coco betaine, oleyl betaine, cocamidopropyl hydroxysultaine, tallowamidopropyl hydroxysultaine, dihydroxyethyl tallow glycinate, cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl)-carboxymethylbetaine, oleyldimethylgamma-carboxy-propylbetaine, lauryl-bis-(2-hydroxypropyl)-carboxy-ethylbetaine, cocodimethylpropylsultaine, stearyldimethylpropylsultaine, laurylbis-( 2-hydroxyethyl)propylsultaine, cocoamidodimethyl-propylsultaine, stearylamidodimethylpropylsultaine, laurylamido-bis-(2-hydroxyethyl) propylsultaine, cocamido disodium 3-hydroxypropyl phosphobetaine, disodium lauriminodipropionate, sodium lauriminodipropionate, disodium tallowiminodipropionate, lauraminopropionate, cocoamphocarboxyglycinate, lauroamphocarboxyglycinate, lauroamphoglycinate, cocoamphopropylsulfonate, lauroamphopropylsulfonate, stearoamphopropylsulfonate, oleoamphopropylsulfonate, capryloamphopropylsulfonate, lauramidopropyl betaine, cocoamphoglycinate, cocoamphopropionate, cocoamphocarboxyglycinate, cocoamphocarboxypropionate, lauroamphoglycinate, lauroamphocarboxyglycinate, lauroamphocarboxypropionate, oleoamphopropionate, caproamphoglycinate, caproamphocarboxyglycinate, caproamphocarboxypropionate, stearoamphoglycinate, isostearoamphopropionate, cocoamphocarboxypropionate, 1-(2-hydroxyethyl)-2-norsoya-2-imidazoline, 1-(2-hydroxyethyl)-2-norcoco-2-imidazoline, 1-(2-hydroxyethyl)-2-[(Z)-8-heptadecyl]-2-imidazoline, dihydroxyethyl tallow glycinate, oleoamphocarboxyglycinate, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl monosodium phosphitaine, lauric myristic amido propyl monosodium phosphitaine, and mixtures thereof. Numerous other amphoteric surfactants are disclosed in U.S. Pat. No. 3,929, 678, the disclosure of which is hereby incorporated by reference.

Preferred amphoteric surfactants for use in the present invention are amine oxides such as those commercially available from Stepan Chemical Company, Northfield, Ill., like cocoamidopropyl dimethylamine oxide (available as AMMONYX® CDO), myristyl cetyl dimethylamine oxide (available as AMMONYX® MCO), and lauryl dimethylamine oxide (available as AMMONYX® LO).

Suitable water-insoluble phosphates for use as an odor-controlling compound in the present invention have a water solubility of less than about 5 grams in 100 milliliters (ml) of water at standard temperature and pressure, preferably less than about 3 grams per 100 ml of water, and more preferably less than about 1 gram per 100 ml of water. Preferably, the water-insoluble phosphate is a water-insoluble hydrogen phosphate, such as an alkaline-earth metal-based hydrogen phosphate, like calcium hydrogen phosphate ($CaHPO_4$), magnesium hydrogen phosphate ($MgHPO_4$), barium hydrogen phosphate ($BaHPO_4$), and hydrates thereof. A highly preferred water-insoluble hydrogen phosphate is calcium hydrogen phosphate ($CaHPO_4$) and hydrates thereof, like calcium hydrogen phosphate hemihydrate and calcium hydrogen phosphate dihydrate. Other useful phosphates and hydrogen phosphates include, but are not limited to, monocalcium phosphate ($Ca(H_2PO_4)_2$), octacalcium phosphate ($Ca_8H_2(PO_4)6$), monomagnesium phosphate ($Mg(H_2PO_4)_2$), $NaAl_3H_{14}(PO_4)_8$, $Na_3Al_2H_{15}(PO_4)_8$, $Na_3Al_{12}H_{15}(PO_4)_8$, $NaAl_3H_{14}(PO_4)_8$, monoiron(III) phosphate ($Fe(H_2PO_4)_3$), $FeH_3(PO_4)_2$, zirconium phosphate ($Zr(HPO_4)_2$), $AlH_3(PO_4)_2$, monoaluminum phosphate ($Al(H_2PO_4)_3$), $Al_2(HPO_4)_3$, aluminum dihydrogen tripolyphosphate ($AlH_2P_3O_{10}$), $Ti(HPO_4)_2$, α-tricalcium phosphate (α-$Ca_3(PO_4)_2$), β-tricalcium phophate (β-$Ca_3(PO_4)_2$), zinc phosphate ($Zn_3(PO_4)_2$), aluminum pyrophosphate ($Al_4(P_2O_7)_3$), calcium dihydrogen pyrophosphate ($Ca_2H_2P_2O_7$), calcium pyrophosphate ($Ca_2P_2O_7$), silicon pyrophosphate ($SiP_2O_7$), titanium pyrophosphate ($TiP_2O_7$), and hydrates thereof.

Another useful odor-controlling compound is the antibacterial compound known as triclosan. Triclosan is a water-insoluble organic molecule having the following formula:

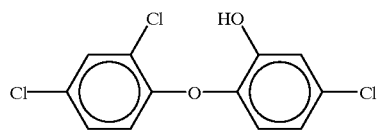

Triclosan is commercially available under the trade-names IRGASAN PG60 (60% active in propylene glycol) and IRGASAN DP300 (100% active), from CIBA-GEIGY Corp., Dyestuffs and Chemicals Div., Greensboro, N.C.

The odor-controlling compound is incorporated into the odor-controlling SAP either during polymerization of the monomers, or after polymerization monomers to form a hydrogel, or both. Triclosan cannot be introduced prior to or during the polymerization step.

Any of the various polymerization initiators that are known for use in preparing SAPs can be used in the present invention. Examples of useful initiators are redox initiators comprising a reducing agent, such as a sulfite or bisulfite of an alkali metal, ammonium sulfite, ammonium metabisulfate, or ammonium bisulfite, a persulfate of an alkali metal or ammonium persulfate; t-butyl hydroperoxide; di-t-butyl hydroperoxide; t-butyl perbenzoate; t-butyl peroxy isopropyl carbonate; and peroxy-3,3,5 trimethylcyclohexane. Examples of suitable thermal initiators include azobisisobutyronitrile; 4-t-butylazo-4'-cyanovaleric acid; 4,4'-azobis(4-cyanovaleric acid); 2,2'-azobis(2-amidinopropane)dihydrochloride; 2,2'-azobis(2,4-dimethylvaleronitrile); dimethyl 2,2'-azobis-isobutyrate; 2,2'-azodimethyl bis(2,4-dimethyl-valeronitrile); (1-phenylethyl)azodiphenylmethane; 2,2'-azobis(2-methylbutyronitrile); 1,1'-azobis(1-cyclohexanecarbonitrile); 2-(carbamoylazo)-isobutyronitrile; 2,2'-azobis(2,4,4-trimethylpenta-2-phenylazo-2,4-dimethyl-4-methoxyvaleronitrile; 2,2'-azobis (2-methylpropane); 2,2'-azobis(N, N'dimethyleneisobutyramidine)dihydrochloride; 4,4'azobis (4-cyanopentanoic acid); 2,2'-azobis(2-methyl-N-[1,1-bis (hydroxymethyl)-2-hydroxyethyl]propionamide); 2,2'-azobis(2-methyl-N-[1,1-bis(hydroxymethyl)ethyl] propionamide); 2,2'-azobis[2-methyl-N(2-hydroxyethyl) propionamide]; 2,2'-azobis(isobutyramide)dihydrate and the like.

These initiators, redox and thermal, can be used singly or in suitable combination. of these, especially preferred initiators are a redox initiator comprising ammonium persulfate and sodium hydrogen sulfite, and azo initiators, such as azobisisobutyronitrile and 2,2'-azobis(2-amidino-propane) dihydrochloride. A suitable initiator for use in the invention is the azoinitiator 2,2'-azobis(2-amidinopropane) dihydrochloride, commercially available under the tradename V-50 from Wako Chemicals U.S.A., Inc., Richmond, Va. The initiator typically is used in the form of an aqueous solution, but the initiator can be diluted with another suitable solvent. The initiator typically is used, for example, in an amount, calculated as solids, of about 0.1% to about 10%, based on the weight of the acrylic acid monomer, preferably about 0.5% to about 5%, based on the weight of the monomer. Depending on the amount and kind of the initiator, the initiator optionally can be used together with isopropyl alcohol, an alkyl mercaptan, or other chain transfer agent to control the molecular weight of the polyacrylic acid to be obtained.

When a thermal and redox initiator are used in combination, the temperature of the monomer solution can vary considerably in accordance with the process of the present invention prior to the addition of the thermal and redox initiators, depending upon the particular thermal initiator added. In any event, the initial temperature of the monomer solution should be below the thermal decomposition temperature of the initiator to avoid premature polymerization initiation; and the temperature of the monomer solution should be sufficiently high such that the redox initiator causes sufficient polymerization at the initial temperature of the monomer solution to raise the temperature of the monomer solution to a level sufficient that the thermal initiator, together with the redox initiator, causes substantially complete polymerization, i.e., leaving less than about 1000 parts per million (ppm) free monomer, and generally less than about 500 ppm free monomer. Free monomer levels less than 200 ppm and even less than 100 ppm have been achieved. The combination of initiators can be added to the mixed monomer solution in a batch process or continuously.

Ultraviolet (UV) light also can be used to effect polymerization of the acrylic acid. UV light can be used in conjunction with a redox initiator and/or a free radical initiator. When UV light is utilized in the polymerization step, a photoinitiator also is added to the reaction mixture. The photoinitiator is used in a standard amount well known to persons skilled in the art. Suitable photoinitiators include, but are not limited to, 2-hydroxy-1-[4-(hydroxyethyoxy) phenyl]-2-methyl-1-propanone, which is commercially available from Ciba Additives of Hawthorne, N.Y., as IRGACURE 2959, and 2-hydroxy-2-methyl-1-phenyl-1-propanone which also is commercially available from Ciba Additives as DAROCUR 1173.

A suitable process for polymerizing the acrylic acid is aqueous solution polymerization, wherein an aqueous solution of acrylic acid and polymerization initiator is subjected to a polymerization reaction and a crosslinking reaction by the addition of a crosslinking agent, such as methylene bisacrylamide. A solution of sodium acrylate (DN about 50 to about 70) also can be polymerized in a similar manner.

The acrylic acid monomer, or salt thereof, preferably is cross-linked concurrently with aqueous solution polymerization to a sufficient extent such that the resulting polymer is water insoluble, but has an ability to absorb several times its weight in water to form a hydrogel. Crosslinking, therefore, renders the resulting polymer substantially water insoluble and, in part, serves to determine the absorption capacity of the polymer. For use in absorption applications, the acidic monomer is lightly crosslinked. Preferably, the polymer has a crosslinking density of less than about 20%, more preferably less than about 10%, and most preferably about 0.01% to about 7%.

A suitable crosslinking agent is used in an amount of less than about 7 wt %, and typically about 0.1 to about 5 wt %, based on the weight of acrylic acid monomer. Examples of crosslinking polyvinyl monomers include, but are not limited to, polyacrylic (or polymethacrylic) acid esters represented by the following formula (I); and bisacrylamides, represented by the following formula (II).

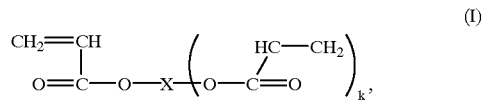
(I)

wherein x is ethylene, propylene, trimethylene, cyclohexyl, hexamethylene, 2-hydroxypropylene, —(CH$_2$CH$_2$O)$_n$CH$_2$CH$_2$—, or

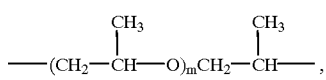

wherein n and m, independently, are an integer 5 to 40, and k is 1 or 2;

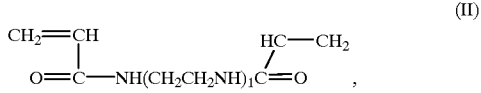

(II)

wherein 1 is 2 or 3.

Specific crosslinking monomers include, but are not limited to, 1,4-butanediol diacrylate, 1,4-butanediol dimethacrylate, 1,3-butylene glycol diacrylate, 1,3-butylene glycol dimethacrylate, diethylene glycol diacrylate, diethylene glycol dimethacrylate, ethoxylated bisphenol A diacrylate, ethoxylated bisphenol A dimethacrylate, ethylene glycol dimethacrylate, 1,6-hexanediol diacrylate, 1,6-hexanediol dimethacrylate, neopentyl glycol dimethacrylate, polyethylene glycol diacrylate, polyethylene glycol dimethacrylate, triethylene glycol diacrylate, triethylene glycol dimethacrylate, tripropylene glycol diacrylate, tetraethylene glycol diacrylate, tetraethylene glycol dimethacrylate, dipentaerythritol pentaacrylate, pentaerythritol tetraacrylate, pentaerythritol triacrylate, trimethylolpropane triacrylate, trimethylolpropane trimethacrylate, tris( 2-hydroxyethyl)isocyanurate triacrylate, tris(2-hydroxyethyl)isocyanurate trimethacrylate, divinyl esters of a polycarboxylic acid, diallyl esters of a polycarboxylic acid, triallyl terephthalate, diallyl maleate, diallyl fumarate, hexamethylenebismaleimide, trivinyl trimellitate, divinyl adipate, diallyl succinate, a divinyl ether of ethylene glycol, cyclopentadiene diacrylate, tetraallyl ammonium halides, or mixtures thereof. Compounds such as divinylbenzene and divinyl ether also can be used as crosslinkers. Especially preferred crosslinking agents are N,N'-methylene-bisacrylamide, N,N'-methylene-bismethacrylamide, ethylene glycol dimethacrylate, and trimethylolpropane triacrylate.

In accordance with one embodiment of the present invention, an aqueous monomer solution can contain the odor-controlling compound, i.e., the cyclodextrin, the amphoteric surfactant, the water-insoluble phosphate, and mixtures thereof, in addition to acrylic acid, crosslinking agent, and water. Triclosan is not added to the monomer solution because triclosan is not sufficiently stable to withstand polymerization conditions. The aqueous monomer solution containing an initiator is exposed to ultraviolet light having an intensity of about 10 to about 30 milliwatts per square centimeter (mW/cm$^2$), for example, for a time period of about 30 seconds to about 20 minutes.

As previously noted, the polymerization reaction proceeds rapidly to yield a highly-viscous hydrogel that is extruded, typically, onto a flat surface such as a continuously-moving conveyor belt. In addition to any odor-controlling compound added to the monomer mixture, additional odor-controlling compound can be admixed with the hydrogel prior to extruding. This admixture then can be extruded, if desired, and neutralized with a base, for example, with sodium carbonate, to provide an extrudate having a degree of neutralization (DN) of about 50% to about 100%, preferably about 65% to about 85%, more preferably about 75% to about 80%. While not intending to be bound by any particular theory, it is believed that odor control is enhanced at lower degrees of neutralization. It is also noted, however, that at lower degrees of neutralization, the liquid absorption and retention properties of the SAP typically are comprised.

Any unreacted free monomer remaining in the viscous hydrogel can be eliminated by addition of sodium metabisulfite, for example. After neutralization, the viscous hydrogel is dehydrated (i.e., dried) to obtain an SAP in a solid or powder form. The dehydration step can be performed by heating the viscous hydrogel to a temperature of about 120° C. for about 1 to about 2 hours in a forced-air oven or by heating the viscous hydrogel overnight at a temperature of about 60° C. The dried solid thereafter can be optionally surface crosslinked with a surface crosslinker, like ethylene glycol diglycidyl ether (i.e., "EGDGE") or propylene glycol.

The odor-controlling SAPs have the odor-controlling compound homogeneously distributed throughout the SAP particle. Depending upon whether the odor-controlling compound is added to the monomer mixture prior to polymerization, or is added to the hydrogel after polymerization, the odor-controlling compound can be physically dispersed throughout the polymer matrix of the SAP particle, or the odor-controlling compound can be either covalently bound to a pendant carboxyl group or grafted or otherwise attached to the polymer, or both.

Typically, if the odor-controlling compound is added to the polymerized hydrogel, then the compound, predominantly, is physically dispersed in the polymer matrix. If the odor-controlling compound is present during the polymerization process, an increased amount of the compound is covalently bound to the polymer, for example, by esterification of a carboxyl group, or by entering the free radical polymerization reaction and grafting to the polymer backbone or becoming a component of the polymer chain. In either case, the odor controlling compound is fixed in the polymer matrix by forces, such as hydrogen bonding or electrostatic forces, which retard or eliminate removal of the odor-controlling compound from the polymer matrix.

The odor-controlling SAP particles of the present invention can be in any form, either regular or irregular, such as granules, fibers, beads, powders, flakes, or foams, or any other desired shape, such as a sheet. In embodiments wherein the odor-controlling SAP is prepared using an extrusion step, the shape of the SAP is determined by the shape of the extrusion die. The shape of the odor-controlling SAP particles also can be determined by other physical operations, such as milling.

In one embodiment, the odor-controlling SAP particles are in the form of a granule or a bead, having a particle size of about 10 to about 10,000 microns ($\mu$m), and preferably about 100 to about 1,000 $\mu$m. To achieve the full advantage of the present invention, the odor-controlling SAP particles have a particle size of about 150 to about 800 $\mu$m.

In another embodiment, the odor-controlling SAP particles are in the shape of a fiber, i.e., an elongated, acicular SAP particle. The fiber can be in the shape of a cylinder, for example, having a minor dimension (i.e., diameter) and a major dimension (i.e., length). The fiber also can be in the form of a long filament that can be woven. Such filament-like fibers have a weight of below about 80 decitex, and preferably below about 70 decitex, per filament, for example, about 2 to about 60 decitex per filament. Tex is the weight in grams per one kilometer of fiber. One tex equals 10 decitex. Poly(acrylic acid) is about 4 decitex.

Cylindrical odor-controlling SAP fibers have a minor dimension (i.e., diameter of the fiber) less than about 1 mm, usually less than about 500 $\mu$m, and preferably less than 250 $\mu$m, down to about 50 $\mu$m. The cylindrical SAP fibers can have a relatively short major dimension, for example, about 1 mm, e.g., in a fibrid, lamella, or flake-shaped article, but generally the fiber has a length of about 3 to about 100 mm. The filament-like fibers have a ratio of major dimension to minor dimension of at least 500 to 1, and preferably at least 1000 to 1, for example, up to and greater than 10,000 to 1.

An odor-controlling SAP thus obtained has an outstanding water-absorbing ability, and is useful for use in sanitary goods, paper diapers, disposable diapers and similar hygienic goods, agricultural or horticultural water-retaining agents, industrial dehydrating agents, sludge coagulants, thickening agents, condensation preventing agents for building materials, release control agents for chemicals and various other applications. Furthermore, a present odor-controlling SAP has a more uniform distribution of an odor-controlling compound throughout the SAP when compared to an SAP that is simply surface coated with an odor-controlling compound, and accordingly, more effectively controls malodors attributed to liquids, such as bodily fluids, like urine, blood, and menses. In addition, odor control is improved because the odor-controlling compound remains in place, or is bound, within the odor-controlling SAP matrix. In contrast, an odor-controlling compound dry blended with particles of an SAP can be easily separated from the SAP particles.

EXAMPLES

The following nonlimiting examples are provided to illustrate the present invention, but are not intended to limit the scope thereof.

Example 1

A monomer mixture containing about 25 to about 28 wt. % acrylic acid, 0.07 mole methylene-bisacrylamide per mole of acrylic acid, 0.061 mole sodium persulfate per mole of acrylic acid, and about 72 to about 75 wt. % water was prepared. To the monomer mixture was added 1 wt. % of a methylated beta-cyclodextrin, which is commercially available under the tradename Beta-Cyclodextrin BW7 M1.8 from Wacker Biochemicals, Adrian, Mich.

The resulting monomer mixture then was polymerized under of UV light. The polymerization was initiated using 0.017 mole DAROCUR 1173 per mole of acrylic acid. The resulting polymer was extruded through a KitchenAid Model K5SS mixer fitted with a meat grinder attachment.

In another example (Example 1A), a portion of the extruded material was admixed with additional methylated beta-cyclodextrin in an amount of about 4 wt. %, based on the weight of the acrylic acid present in the initial monomer mixture. Then the mixture was extruded a second time. The twice-extruded polymer was treated with granular sodium carbonate to provide a neutralized polymer having a degree of neutralization (DN) of about 75%. Subsequently, the polymer was extruded a third time, and then treated with sodium metabisulfite to remove residual monomers. The resulting extrudate was dried in a forced-air oven at 120° C. for about 1 to 2 hours, then ground and sized through sieves to obtain a desired particle size (e.g., about 180 to about 710 microns). Alternatively, the extrudate can be dried overnight at a temperature of about 60° C. After drying and sizing, the particles were coated and surface crosslinked with 600 parts per million (ppm) of ethylene glycol diglycidyl ether, i.e., EGDGE.

Example 2

A monomer mixture containing about 25 to about 28 wt. % acrylic acid, 0.07 mole methylene-bisacrylamide per mole of acrylic acid, 0.061 mole sodium persulfate per mole of acrylic acid, and about 72 to about 75 wt. % water was prepared. To the monomer mixture was added about 0.005 to about 0.14 mol % (i.e., about 1 to about 10 wt. %) of beta-cyclodextrin having a 1.8 degree of substitution with monochlorotriazine (MCT). The cyclodextrin derivative was obtained commercially under the tradename Beta-Cyclodextrin BW7 MCT from Wacker Biochemicals.

The resulting monomer mixture then was polymerized under UV light. The polymerization was initiated using about 0.017 mole DAROCUR 1173 per mole of acrylic acid. The resulting polymer was extruded, and then treated with additional beta-cyclodextrin (MCT) in an amount of about 4 wt. % based on the weight of the acrylic acid present in the initial monomer mixture. Then, the polymer was extruded a second time. The twice-extruded polymer was treated with granular sodium carbonate to achieve a degree of neutralization (DN) of about 75%. The resulting extrudate was dried in a forced-air oven at 120° C. for about 1 to 2 hours, then ground and sized through sieves to obtain a desired particle size. After drying and sizing, the particles were surface crosslinked with 600 ppm of EGDGE.

The beta-cyclodextrin MCT provided additional strength to the SAP, while "locking" the odor controlling compound uniformly into the SAP.

Example 3

A monomer mixture containing about 25 to about 28 wt. % acrylic acid, 0.07 mole methylene-bisacrylamide per mole of acrylic acid, 0.061 mole sodium persulfate per mole of acrylic acid, and about 72 to about 75 wt. % water was prepared. To the monomer mixture was added 6 wt. % of technical grade beta-cyclodextrin, which was obtained commercially under the tradename Beta-Cyclodextrin BW7 tech. gr. from Wacker Biochemicals.

The resulting monomer mixture was polymerized under UV light. The polymerization was initiated using 0.017 mole DAROCUR 1173 per mole of acrylic acid. The resulting polymer was extruded, and treated with additional technical grade beta-cyclodextrin in an amount of about 2 wt. % based on the weight of the acrylic acid present in the initial monomer mixture. Then, the polymer was extruded a second time. The twice-extruded polymer was treated with granular sodium carbonate to provide a neutralized polymer having a degree of neutralization (DN) of about 50% to about 75%. The resulting extrudate was dried in a forced-air oven at a temperature of about 110° C. to about 178° C. for about one hour, preferably about 120° C. for about 1 to 2 hours, then ground and sized through sieves to obtain a desired particle size. At drying temperatures in excess of 178° C., the particles discolored. After drying and sizing, the particles were surface crosslinked with 600 ppm of EGDGE.

Example 4

Ten monomer mixtures each containing about 57 to about 58 wt. % acrylic acid, 0.007 mole trimethylpropane triacrylate per mole of acrylic acid, and about 42 to about 43 wt. % water were prepared. The acrylic acid was neutralized to DN about 60 by addition of a base, like sodium carbonate. To the individual monomer mixtures was added 1 wt. % up to 10 wt % (in increments of 1 wt. %) of technical grade beta-cyclodextrin, which was obtained commercially under the tradename Beta-Cyclodextrin BW7 from Wacker Biochemicals.

The polymerizations were initiated using about 0.034 mole of an azoinitiator (e.g., V-50) per mole of acrylic acid and 0.061 mole sodium persulfate per mole of acrylic acid. A redox initiator containing a mixture of 33% sodium persulfate and 33% sodium metabisulfite was used to begin the polymerization. The exothermic polymerization yields a nearly dry, hard polymer slab. The resulting polymers, in slab form, were dried in a forced-air oven at 60° C. overnight, then ground in a mill and sized through sieves to obtain a desired particle size. After drying and sizing, the particles were surface crosslinked with 600 ppm of EGDGE.

Individually, about 0.5 grams of each of the odor-controlling SAP particles then were combined with about 30 milliliters of urine. The odor-controlling SAPs of Example 4 incorporating the beta-cyclodextrin effectively trapped ammonia and urea particles, and significantly reduced the malodors associated with urine and urine degradation. A sniff-test panel of five individuals selected an odor-controlling SAP containing about 5% beta-cyclodextrin as the most efficacious composition.

Example 5

A monomer mixture containing about 25 to about 28 wt. % acrylic acid, 0.07 mole methylene-bisacrylamide per mole of acrylic acid, 0.061 mole sodium persulfate per mole of acrylic acid, and about 72 to about 75 wt. % water was prepared. To the monomer mixture was added about 1 to about 4.4 wt. % of alpha-cyclodextrin, which was obtained commercially under the tradename ALPHA W6 TECHNICAL POWDER from Wacker Biochemicals.

The resulting monomer mixture was polymerized under UV light. The polymerization was initiated using about 0.017 mole DAROCUR 1173 per mole of acrylic acid. The resulting polymer was extruded, and treated with additional alpha-cyclodextrin in an amount of about 5 wt. % based on the weight of the acrylic acid present in the initial monomer mixture. Then, the polymer was extruded a second time. The twice-extruded polymer was treated with granular sodium carbonate to provide a neutralized polymer having a degree of neutralization (DN) of about 50% to about 100%. The resulting extrudate was dried in a forced-air oven at a temperature of about 110° C. to about 178° C. for about one hour, preferably about 120° C. for about 1 to 2 hours, then ground and sized through sieves to obtain a desired particle size. After drying and sizing, the particles were surface crosslinked with 600 ppm of EGDGE.

The odor-controlling SAP of Example 5 incorporates alpha-cyclodextrin as the odor-controlling compound. Alpha-cyclodextrin has a smaller interior cavity than the beta-cyclodextrin utilized in Example 4. It was observed that the smaller interior cavity of the alpha-cyclodextrin of Example 5 trapped ammonia molecules more effectively than the beta-cyclodextrin of Example 4.

Example 6

A monomer mixture containing about 25 to about 28 wt. % acrylic acid, 0.07 mole methylene-bisacrylamide per mole of acrylic acid, 0.061 mole sodium persulfate per mole of acrylic acid, and about 72 to about 75 wt. % water was prepared. To the monomer mixture was added 1 wt. % to 4.4 wt. % of gamma-cyclodextrin, which was obtained commercially under the tradename GAMMA W8 TECHNICAL POWDER from Wacker Biochemical.

The resulting monomer mixture then was polymerized under UV light. The polymerization was initiated using about 0.017 mole DAROCUR 1173 per mole of acrylic acid. The resulting polymer was extruded, and treated with additional gamma-cyclodextrin in an amount of about 1 wt. % based on the weight of the acrylic acid present in the initial monomer mixture. Then, the polymer was extruded a second time. The twice-extruded polymer was treated with granular sodium carbonate to provide a neutralized polymer having a degree of neutralization (DN) of about 50% to about 100%. The resulting extrudate was dried in a forced-air oven at a temperature of about 110° C. to about 178° C. for about one hour, preferably about 120° C. for about 1 to 2 hours, then ground and sized through sieves to obtain a desired particle size. After drying and sizing, the particles were surface crosslinked with 600 ppm of EGDGE.

The odor-controlling SAP of Example 6 incorporates gamma-cyclodextrin as the odor-controlling compound. Gamma-cyclodextrin has a larger interior cavity than the beta- and alpha-cyclodextrins utilized in Examples 4 and 5, respectively. It was observed that the larger interior cavity of the gamma-cyclodextrin of Example 6 effectively trapped ammonia molecules, however, not as effectively as the smaller interior cavity of the odor-controlling SAPs formed in Examples 4 and 5 using the beta- and alpha-cyclodextrin, respectively.

Additional odor-controlling SAPs of the present invention were prepared and their ability to inhibit ammonia odor and/or formation were determined. In particular, the following Examples 7–16 were prepared and tested for ammonia inhibition by the following method.

Ammonia Inhibition Measurement Method for Examples 7–16

The amount of ammonia released from the odor-controlling SAPs prepared in Examples 7–16 was measured by placing 0.2 grams of the SAP into a testing apparatus consisting of a 250 milliliter (ml) three-necked round-bottom flask fitted with a 125 ml pressure equalizing addition funnel, a stop-cock with a vacuum adapter, and a thermometer. A partial vacuum was drawn on the testing apparatus using a sink aspirator for about two minutes. Then, the stopcock was closed and 50 ml of a 1000 ppm ammonia standard solution was added into the flask to hydrate the SAP. The SAP was gently swirled with the ammonia solution, then the ammonia solution was allowed to hydrate the SAP for about ten minutes.

The flask was immersed in a 37.9° C. water bath such that the water level reached the bottom of each of the flask necks. When the gas temperature within the flask reached about 30° C., a time period of five minutes was allowed to elapse. Then, the vacuum was broken, the thermometer was removed, and a Dragger pump with an Ammonia 5/a Dragger tube was used in accordance with manufacturer's instructions to measure the headspace concentration of ammonia present in the flask at about 2 millimeters (mm) below the flask neck.

Ammonia inhibition was measured by the following ratio:

ppm of ammonia released from a control SAP ppm of ammonia released from experimental SAP.

A control SAP was a standard, lightly-crosslinked polyacrylic acid product, neutralized 75% to 80%, that was free of an odor-controlling compound. In particular, the control SAP was essentially identical to the SAP of Example 1 with the exception that the SAP was free of cyclodextrin. Thus, the relative ammonia inhibition of the control SAP was 1.

Example 7

An odor-controlling SAP was prepared according to the procedure generally described in Example 1, wherein the odor-controlling compound was added only to the monomer mixture prior to polymerization. The odor-controlling SAP of Example 7, however, included calcium hydrogen phosphate as the odor-controlling compound, as opposed to a cyclodextrin. The calcium hydrogen phosphate was included in the monomer mixture in an amount of about 1 wt. % based on the weight of the acrylic acid in the monomer mixture. The monomer mixture was polymerized under UV light for about 8.5 minutes.

The odor-controlling SAP of Example 7 exhibited a relative ammonia inhibition of about 1.75, i.e., about 75% better inhibition than the control SAP. The liquid absorbency and retention of the odor-controlling SAP of Example 7 was slightly improved over the control SAP.

Example 8

An odor-controlling SAP was prepared according to the procedure generally described in Example 1, wherein the odor-controlling compound was added only to the unneutralized polyacrylic acid hydrogel prior to extrusion and neutralization. Like Example 7, the odor-controlling compound was calcium hydrogen phosphate. The calcium hydrogen phosphate was included in a preneutralized polyacrylic acid hydrogel in an amount of about 1 wt. % based on the weight of the acrylic acid in the monomer mixture. The monomer mixture was exposed and polymerized under the UV light for about 8.5 minutes.

The odor-controlling SAP of Example 8 exhibited a relative ammonia inhibition of about 1.2, i.e., about 20% better inhibition than the control SAP. The liquid absorbency and retention of the odor-controlling SAP of Example 8 was essentially equal to the control SAP.

Example 9

An odor-controlling SAP was prepared according to the procedure described in Example 7. However, the odor-controlling compound was an amphoteric surfactant, i.e., lauryl dimethylamine oxide obtained commercially under the tradename AMMONYX® LO from Stepan Chemical Co., Northfield, Ill., as opposed to calcium hydrogen phosphate. The amphoteric surfactant was included in the monomer mixture in an amount of about 1 wt. % based on the weight of the acrylic acid in the monomer mixture. The monomer mixture was exposed and polymerized under the UV light for about 10.5 minutes.

The odor-controlling SAP of Example 9 exhibited a relative ammonia inhibition of about 2.25, i.e., about 125% better inhibition than the control SAP.

Example 10

An odor-controlling SAP was prepared according to the procedure generally described in Example 8. The odor-controlling compound was AMMONYX® LO. The amphoteric surfactant was included in the preneutralized polyacrylic acid hydrogel in an amount of about 1 wt. % based on the weight of the acrylic acid in the monomer mixture. The monomer mixture was exposed and polymerized under the UV light for about 8.5 minutes.

The odor-controlling SAP of Example 10 exhibited a relative ammonia inhibition of about 2, i.e., about 100% better inhibition than the control SAP.

Example 11

An odor-controlling SAP was prepared according to the procedure generally described in Example 8. The odor-controlling compound was a mixture of calcium hydrogen phosphate and beta-cyclodextrin. The calcium hydrogen phosphate and beta-cyclodextrin each were included in the preneutralized polyacrylic acid hydrogel in an amount of about 4 wt. % based on the weight of the acrylic acid in the monomer mixture. The monomer mixture was exposed and polymerized under the UV light for about 8.5 minutes.

The odor-controlling SAP of Example 11 exhibited a relative ammonia inhibition of about 2.5, i.e., about 150% better inhibition than the control SAP.

Example 12

An odor-controlling SAP was prepared according to the procedure generally described in Example 8. The odor-controlling compound was beta-cyclodextrin BW7 M1.8, which was obtained from Wacker Biochemicals. The beta-cyclodextrin was included in the preneutralized polyacrylic acid hydrogel in an amount of about 4 wt. % based on the weight of the acrylic acid in the monomer mixture. The monomer mixture was exposed and polymerized under the UV light for about 8.5 minutes.

The odor-controlling SAP of Example 12 exhibited a relative ammonia inhibition of about 2.4, i.e., about 140% better inhibition than the control SAP.

Example 13

An odor-controlling SAP was prepared according to the procedure generally described in Example 8. The odor-controlling compound was beta-cyclodextrin BW7 MCT, which was obtained from Wacker Biochemicals. The beta-cyclodextrin derivative was included in the preneutralized polyacrylic acid hydrogel in an amount of about 4 wt. % based on the weight of the acrylic acid in the monomer mixture. The monomer mixture was exposed and polymerized under the UV light for about 8.5 minutes.

The odor-controlling SAP of Example 13 exhibited a relative ammonia inhibition of about 1.75, i.e., about 75% better inhibition than the control SAP.

Example 14

An odor-controlling SAP was prepared according to the procedure generally described in Example 8. The odor-controlling compound was a technical grade beta-cyclodextrin, which was obtained from Wacker Biochemicals under the tradename Beta-Cyclodextrin BW7 tech. gr. The beta-cyclodextrin was included in the preneutralized polyacrylic acid hydrogel in an amount of about 4 wt. % based on the weight of the acrylic acid in the monomer mixture. The monomer mixture was exposed and polymerized under the UV light for about 8.5 minutes.

The odor-controlling SAP of Example 14 exhibited a relative ammonia inhibition of about 2.25, i.e., about 125% better inhibition than the control SAP.

Example 15

An odor-controlling SAP was prepared according to the procedure generally described in Example 8. The odor-controlling compound was a calcium phosphate, as opposed to calcium hydrogen phosphate. The calcium phosphate was included in the preneutralized polyacrylic acid hydrogel in an amount of about 1 wt. % based on the weight of the acrylic acid in the monomer mixture. The monomer mixture was exposed and polymerized under the UV light for about 8.5 minutes.

The odor-controlling SAP of Example 15 exhibited a relative ammonia inhibition of about 1.75, i.e., about 75% better inhibition than the control SAP.

Example 16

An odor-controlling SAP was prepared according to the procedure described in Example 7. However, the odor-controlling compound was calcium phosphate, as opposed to calcium hydrogen phosphate. The calcium phosphate was included in the monomer mixture in an amount of about 1 wt. % based on the weight of the acrylic acid in the monomer mixture. The monomer mixture was exposed and polymerized under the UV light for about 8.5 minutes.

The odor-controlling SAP of Example 16 exhibited a relative ammonia inhibition of about 2.8, i.e., about 180% better inhibition than the control SAP.

Example 17

Five samples of an odor-controlling SAP were prepared according to the procedure generally described in Example 8. The odor-controlling compound was triclosan, which was obtained from Ciba-Geigy Corp., under the tradename IRGASAN DP300. The triclosan was added simultaneously with sodium carbonate into individual samples of a polyacrylic acid hydrogel in amount of about 0.1 wt. %, 0.2 wt. %, 0.3 wt. %, 0.5 wt. %, and 1.0 wt. %, based on the weight of the acrylic acid in the monomer mixture.

Each of the five SAP samples was analyzed after each processing step for triclosan content and antimicrobial efficacy using assay methods known to persons skilled in the art. The tests indicated triclosan did not degrade. It is theorized that interactions between the triclosan and the polyacrylic acid extrudate serve as a time release mechanism for the triclosan. Efficacy testing indicated that the odor-controlling SAP samples exhibited excellent antimicrobial activity against gram positive *Staphylococcus aureus* (AATC 9144), gram negative *Escheria Coli* (NTC 8196), and gram negative *Proteus vulgaris* (ATCC 6896).

Example 18 (Comparative Example)

Two odor-controlling SAPs were prepared using a dry blending technique wherein a technical grade beta-cyclodextrin was dry blended with a surface-crosslinked SAP (crosslinked with 600 ppm of EGDGE) in amount of about 2 wt. % and 4 wt. %. The beta-cyclodextrin had a particle size of about 100 to about 200 microns, and average particle size of about 150 microns.

One of the odor-controlling SAPs of Example 18 (2 wt. % cyclodextrin) exhibited a relative ammonia inhibition of about 1.07, i.e., about 7% better inhibition than the control SAP, while the other odor-controlling SAP (4 wt. % cyclodextrin) exhibited a relative ammonia inhibition of about 1.15, i.e., about 15% better inhibition than the control SAP. While an improvement in ammonia inhibition was observed, the improvement was significantly less than the improvements obtained with the odor-controlling SAPs made in accordance with the present invention, wherein the odor-controlling compound is homogeneously distributed throughout the SAP particle.

The relatively poor performance of the odor-controlling SAPs of comparative Example 18 can be attributed to the method by which the cyclodextrin is incorporated into a blend with the SAP. Furthermore, it is theorized that, in part, due to the method of incorporating the cyclodextrin into the odor-controlling SAPs of Example 18 (i.e., simple dry blending of SAP particles and cyclodextrin particles), there is an insufficient time for solubilization of the cyclodextrin because the SAP quickly absorbs the liquid. As previously described, insufficient solublization of the cyclodextrin inhibits the efficacy of the cyclodextrin to encapsulate ammonia and urea molecules.

Example 19

Odor-controlling SAPs were prepared according to the procedure generally described in Examples 7 and 8. The odor-controlling compound used in the SAPs of Example 19 was an amphoteric surfactant obtained under the tradename AMMONYX® LO from Stepan Chemical Company, Northfield, Ill.

A number of SAPs were prepared using 0.1 to 10 wt. % of the amphoteric surfactant. The amphoteric surfactant was added either in the monomer mixture in accordance with the procedure generally described in Example 7, or to the polyacrylic acid hydrogel in accordance with the procedure generally described in Example 8. The hydrogels then were neutralized to a degree of neutralization of 50%, 60%, or 75%. The neutralized hydrogels were dried to provide odor-controlling SAP particles of the present invention. The measured relative ammonia inhibition of each of the odor-controlling SAPs of Example 19 are provided below in Table I. It can be seen that the relative ammonia inhibition is superior to that of the control SAP in each instance.

TABLE I

| Amount amphoteric surfactant | 50% DN (Monomer Addition) | 50% DN (Hydrogel Addition) | 60% DN (Monomer Addition) | 60% DN (Hydrogel Addition) | 75% DN (Monomer Addition) | 75% DN (Hydrogel Addition) |
| --- | --- | --- | --- | --- | --- | --- |
| 2 wt. % | 20.91 | 4.42 | 6.97 | 6.97 | 1.41 | 8.71 |
| 4 wt. % | 8.96 | 19.6 | 5.06 | 20.36 | 3.56 | 2.8 |
| 6 wt. % | 1.69 | 8.48 | 13.07 | 9.22 | 13.63 | 2.15 |

For purposes of comparison, additional odor-controlling SAPs were prepared by blending the amphoteric surfactant (AMMONYX® LO) with a surface-crosslinked SAP (crosslinked with 600 ppm of EGDGE). The amphoteric surfactant was admixed with the SAP in amount of about 2 wt. % and 4 wt. %, based on the weight of the acrylic acid in the monomer mixture. These two odor-controlling SAPs exhibited a relative ammonia inhibition of about 0.93, i.e., an about 7% decrease in inhibition than the control SAP, and 1.11, i.e., an about 11% improved inhibition than the control SAP. These results should be compared to the results in Table I, which show a substantial increase in ammonia inhibition. This comparison illustrates the unexpected results achieved by homogeneously distributing an odor-controlling compound throughout the SAP particle, as opposed to admixing the odor-controlling compound with the SAP or applying the odor-controlling compound to the surface of the SAP.

The foregoing description is given for clearness of understanding only, and no unnecessary limitations should be understood therefrom, as modifications within the scope of the invention can be apparent to those skilled in the art.

What is claimed is:

1. An odor-controlling superabsorbent polymer particle comprising a superabsorbent polymer and an odor-controlling compound selected from the group consisting of a cyclodextrin compound, triclosan, an amphoteric surfactant, a water-insoluble phosphate, and mixtures thereof, wherein the odor-controlling compound is homogeneously distributed throughout the particle.

2. The particle of claim 1 wherein the superabsorbent polymer comprises a polymerized α,β-unsaturated carboxylic acid or salt thereof.

3. The particle of claim 2 wherein the α,β-unsaturated carboxylic acid is selected from the group consisting of acrylic acid, methacrylic acid, ethacrylic acid, α-chloroacrylic acid, α-cyanoacrylic acid, β-methylacrylic acid, α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, fumaric acid, tricarboxyethylene, maleic anhydride, and mixtures thereof.

4. The particle of claim 2 wherein the α,β-unsaturated carboxylic acid has a degree of neutralization of 0 to 100.

5. The particle of claim 4 wherein the α,β-unsaturated carboxylic acid has a degree of neutralization of about 50 to about 100.

6. The particle of claim 1 wherein the superabsorbent polymer is selected from the group consisting of polyacrylic acid, a hydrolyzed starchacrylonitrile graft copolymer, a starch-acrylic acid graft copolymer, a saponified vinyl acetate-acrylic ester copolymer, a hydrolyzed acrylonitrile copolymer, a hydrolyzed acrylamide copolymer, an ethylene-maleic anhydride copolymer, an isobutylene-maleic anhydride copolymer, a poly(vinylsulfonic acid), a poly(vinylphosphonic acid), a poly(vinylphosphoric acid), a poly(vinylsulfuric acid), a sulfonated polystyrene, and mixtures thereof.

7. The particle of claim 1 wherein the superabsorbent polymer is selected from the group consisting of a poly(vinylamine), a poly(dialkylaminoalkyl (meth)acrylamide), a polyethylenimine, a poly(allylamine), a poly(allylguanidine), a poly(dimethyldiallylammonium hydroxide), a quaternized polystyrene derivative, a guanidine-modified polystyrene, a quaternized poly((meth)acrylamide) or ester analog, a poly(vinylguanidine), and mixtures thereof.

8. The particle of claim 1 wherein the cyclodextrin compound comprises an alpha-cyclodextrin, a beta-cyclodextrin, a gamma-cyclodextrin, a cyclodextrin derivative, a cyclodextrin copolymer, or mixtures thereof.

9. The particle of claim 8 wherein the cyclodextrin derivative comprises methyl-beta-cyclodextrin, hydroxyethyl-beta-cyclodextrin, hydroxypropyl-beta-cyclodextrin, a monochlorotriazine-substituted cyclodextrin, or mixtures thereof.

10. The particle of claim 1 wherein the water-insoluble phosphate has a water solubility of less than about 5 grams in 100 milliliters of water at standard temperature and pressure.

11. The particle of claim 1 wherein the water-insoluble phosphate is an alkaline-earth metal-based hydrogen phosphate selected from the group consisting of calcium hydrogen phosphate, magnesium hydrogen phosphate, barium hydrogen phosphate, and hydrates and mixtures thereof.

12. The particle of claim 1 wherein the water-insoluble phosphate is selected from the group consisting of monocalcium phosphate, octacalcium phosphate, monomagnesium phosphate, $NaAl_3H_{14}(PO_4)_8$, $Na_3Al_2H_{15}(PO_4)_8$, $Na_3Al_{12}H_{15}(PO_4)_8$, $NaAl_3H_{14}(PO_4)_8$, monoiron(III) phosphate, $FeH_3(PO_4)_2$, zirconium phosphate, $AlH_3(PO_4)_2$, monoaluminum phosphate, $Al_2(HPO_4)_3$, aluminum dihydrogen tripolyphosphate, $Ti(HPO_4)_2$, α-tricalcium phosphate, β-tricalcium phophate, zinc phosphate, aluminum pyrophosphate, calcium dihydrogen pyrophosphate, calcium pyrophosphate, silicon pyrophosphate, titanium pyrophosphate, and hydrates and mixtures thereof.

13. The particle of claim 1 wherein the amphoteric surfactant is selected from the group consisting of a betaine, a hydroxypropylsultaine, an amine oxide, an n-alkylaminopropionate, an n-alkyliminodipropionate, a phosphobetaine, a phosphitaine, an imidazoline, an alkoamphopropionate, an alkoamphocarboxypropionate, an alkoamphopropylsulfonate, an alkoamphoglycinate, an alkoamphocarboxyglycinate, and mixtures thereof.

14. The particle of claim 1 wherein the amphoteric surfactant is an amine oxide.

15. The particle of claim 14 wherein the amine oxide comprises cocoamidopropyl dimethylamine oxide, myristyl cetyl dimethylamine oxide, lauryl dimethylamine oxide, or mixtures thereof.

16. The particle of claim 1 wherein the odor-controlling compound is present in an amount of about 0.1% to about 10% by weight, based on the weight of the superabsorbent polymer.

17. The particle of claim 16 wherein the odor-controlling compound is present in an amount of about 1% to about 8% by weight, based on the weight of the superabsorbent polymer.

18. The particle of claim 16 wherein the odor-controlling compound is present in an amount of about 3% to about 5% by weight, based on the weight of the superabsorbent polymer.

19. The particle of claim 1 wherein triclosan is present in an amount of about 0.1% to about 1% by weight, based on the weight of the superabsorbent polymer.

20. The particle of claim 1 having a relative ammonia inhibition of at least about 1.2 compared to a superabsorbent polymer free of the odor-controlling compound.

21. The particle of claim 20 having a relative ammonia inhibition of at least about 1.75 compared to the superabsorbent polymer free of the odor-controlling compound.

22. The particle of claim 1 wherein the odor-controlling compound is present in the particle as individual domains of about 25 to about 200 microns in diameter.

23. The particle of claim 1 wherein the superabsorbent polymer comprises polyacrylic acid neutralized about 50% to about 100%.

24. An article comprising the odor-controlling superabsorbent polymer particle of claim 1.

25. The article of claim 24 selected from the group consisting of a diaper and a catamenial device.

26. A method of manufacturing an odor-controllig superabsorbent polymer comprising the steps of:
 (a) forming a mixture comprising water and a vinyl monomer;
 (b) polymerizing the mixture to form a hydrogel;
 (c) admixing the hydrogel formed in step (b) with an odor-controlling compound selected from the group consisting of a cyclodextrin compound, triclosan, an amphoteric surfactant, a water-insoluble phosphate, and mixtures thereof; and,
 (d) optionally, neutralizing the hydrogel admixture formed in step (c).

27. The method of claim 26 further comprising the step of:
 (e) drying the hydrogel.

28. The method of claim 26 wherein the odor-controlling compound is homogeneously distributed throughout the hydrogel in step (c).

29. The method of claim 26 wherein the vinyl monomer comprises an α,β-unsaturated carboxylic acid or a salt thereof.

30. The method of claim 26 wherein the α,β-carboxylic acid is neutralized to DN about 50 to 100 prior to polymerizing in step (b).

31. The method of claim 26 wherein the odor-controlling compound is present in an amount of about 0.1% to about 10% by weight, based on the weight of the vinyl monomer present in step (a).

32. The method of claim 26 wherein the odor-controlling compound is admixed with the hydrogel by extruding a mixture of the odor-controlling compound and the hydrogel.

33. The method of claim 26 wherein the hydrogel mixture is neutralized about 50% to about 100% in step (d).

34. The method of claim 26 wherein the α,β-unsaturated carboxylic acid comprises acrylic acid.

35. The method of claim 34 wherein the odor-controlling compound comprises a cyclodextrin compound.

36. The method of claim 34 wherein the odor-controlling compound comprises triclosan.

37. The method of claim 34 wherein the odor-controlling compound comprises an amphoteric surfactant.

38. The method of claim 34 wherein the odor-controlling compound comprises a water-insoluble phosphate.

39. An odor-controlling superabsorbent polymer prepared by the method of claim 26.

40. A method of manufacturing an odor-controlling superabsorbent polymer comprising the steps of:

(a) forming a mixture comprising water, a vinyl monomer, and an odor-controlling compound selected from the group consisting of a cyclodextrin compound, an amphoteric surfactant, a water-insoluble phosphate, and mixtures thereof;

(b) polymerizing the mixture to form a hydrogel;

(c) optionally, admixing the polymeric hydrogel formed in step (b) with a second odor-controlling compound selected from the group consisting of a cyclodextrin compound, triclosan, an amphoteric surfactant, a water-insoluble phosphate, and mixtures thereof; and, (d) optionally, neutralizing the unneutralized hydrogel.

41. The method of claim 40 further comprising the step of:

(e) drying the hydrogel.

42. The method of claim 40 wherein the odor-controlling compound is homogeneously distributed throughout the polymer.

43. The method of claim 40 wherein the vinyl monomer comprises an α,β-unsaturated carboxylic acid or a salt thereof.

44. The method of claim 43 wherein the α,β-unsaturated carboxylic acid comprises acrylic acid.

45. The method of claim 43 wherein the α,β-carboxylic acid is neutralized to DN about 50 to 100 prior to polymerizing in step (b).

46. The method of claim 40 wherein the second odor-controlling compound is admixed with the hydrogel by extruding a mixture of the second odor-controlling compound and the hydrogel of step (b).

47. The method of claim 40 wherein the hydrogel mixture is neutralized about 50% to about 100% in step (d).

48. An odor-controlling superabsorbent polymer prepared by the method of claim 40.

* * * * *